(12) United States Patent
Weinberg et al.

(10) Patent No.: US 11,517,607 B2
(45) Date of Patent: Dec. 6, 2022

(54) PROTECTIVE EFFECTS OF OIL PALM COMPOSITION ON ALZHEIMER'S DISEASE

(71) Applicant: Malaysian Palm Oil Board, Selangor (MY)

(72) Inventors: Robert P. Weinberg, Cambridge, MA (US); Chokyun Rha, Cambridge, MA (US); Anthony J. Sinskey, Cambridge, MA (US); Yew Ai Tan, Selangor Darul Ehsan (MY); Ravigadevi Sambanthamurthi, Selangor Darul Ehsan (MY)

(73) Assignee: MALAYSIAN PALM OIL BOARD, Kajang (MY)

( * ) Notice: Subject to any disclaimer, the term of this patent is extended or adjusted under 35 U.S.C. 154(b) by 0 days.

(21) Appl. No.: 16/507,838

(22) Filed: Jul. 10, 2019

(65) Prior Publication Data

US 2020/0085903 A1    Mar. 19, 2020

Related U.S. Application Data

(63) Continuation of application No. 15/028,265, filed as application No. PCT/MY2014/000252 on Oct. 10, 2014.

(30) Foreign Application Priority Data

Oct. 11, 2013  (MY) .......................... PI 2013003739

(51) Int. Cl.
*A61K 36/889*  (2006.01)
*A23D 9/007*  (2006.01)
*A23L 33/115*  (2016.01)
*A23L 33/105*  (2016.01)
*A61K 36/00*  (2006.01)

(52) U.S. Cl.
CPC ............ *A61K 36/889* (2013.01); *A23D 9/007* (2013.01); *A23L 33/105* (2016.08); *A23L 33/115* (2016.08); *A61K 2236/15* (2013.01)

(58) Field of Classification Search
None
See application file for complete search history.

(56) References Cited

FOREIGN PATENT DOCUMENTS

WO    WO2010087693 A1 *  5/2010

OTHER PUBLICATIONS

Leow et al. ("Oil palm phenolics confer neuroprotective effects involving cognitive and motor functions in mice" Nutritional Neuroscience, vol. 16, No. 5, pp. 207-217 (Sep. 2013)). (Year: 2013).*

* cited by examiner

*Primary Examiner* — Michael Barker
*Assistant Examiner* — Randall O Winston
(74) *Attorney, Agent, or Firm* — Maschoff Brennan (57) ABSTRACT

Present invention discloses an oil palm composition for use in prevention or treatment of Alzheimer's disease. The composition is useful in impeding formation of neurotoxic peptide. Present invention can be used in preparation of a medicament in a therapeutic effective amount for prevention or treatment of Alzheimer's disease and diseases related thereto.

4 Claims, 4 Drawing Sheets

OPP impedes aggregation of beta-amyloid peptide

Beta amyloid incubated with buffer

FIG. 4A

Beta amyloid incubated with OPP

PROTECTIVE EFFECTS OF OIL PALM COMPOSITION ON ALZHEIMER'S DISEASE

RELATED APPLICATIONS

The present application is a Continuation of U.S. application Ser. No. 15/028,265 filed Apr. 8, 2016 entitled "Protective Effects of Oil Palm Composition on Alzheimer's Disease", which is a national stage filing under 35 U.S.C. § 371 of PCT/MY2014/000252 filed Oct. 20, 2014, the contents of all of which are herein incorporated by reference in their entireties.

FIELD OF THE INVENTION

The present invention relates to a composition with protective effects treating Alzheimer's disease. More particularly, relates to the use of palm oil-based phenolics in impeding β-amyloid peptide aggregation.

BACKGROUND OF THE INVENTION

Alzheimer's disease (AD) is an incurable neurodegenerative disease that progressively worsened and eventually led to death. AD is often diagnosed in persons over the age of 65 years and has affected 36 million persons globally in 2010. At the current rate of increase in prevalence, it is predicted that AD will affect 1 in 85 persons worldwide by the year 2050.

The onset of AD often shows symptoms that appear to be "age-related" issues and difficulties in coping with stress. During the early stage, there is difficulty with acquiring new memories so that it is difficult to recall recent events. As AP progressed to worsened, one observes confusion, irritability, aggression, language breakdown, mood swings, long-term memory loss, and the withdrawal of the person from society while their senses decline.

The cause of AD is yet to be determined, however there are various hypothesis explaining the cause of this disease. One of the hypotheses proposed is Amyloid hypothesis, which is used in present invention. Amyloid hypothesis discloses the pathogenesis of AD to be essentially-related to beta amyloid peptide (BAP) (MW 4514 Da). Amyloid beta is a peptide composed of 36-43 amino acids, which is processed from a transmembrane cellular glycoprotein amyloid precursor protein (APP). An autosomal dominant mutation in the APP results in a hereditary form of early-onset Alzheimer's disease, with increase in amyloid beta peptide. The amyloid beta peptide can form dimers which are quite toxic to neurons.

One of the experimental evidences supporting Amyloid hypothesis is from the genetic locus of the amyloid beta precursor protein (APP) on chromosome 21, patient with Down's syndrome (Trisomy 21) will have an extra gene copy for the APP, it is observed that these patients universally succumb to AD by the age of 40 years. In addition, inheritable AD is also speculated to be involved with APOE4. This allelotype results in an excessive accumulation of beta amyloid in the brain, preceding the very early appearance of AD at only 40 years of age. Another research on transgenic mice expressing a mutation of the human APP gene shows that these mice develop fibrillar deposits of amyloid peptide in the brain and develop Alzheimer's-like neuropathology with specific spatial learning deficits.

Figure 1:
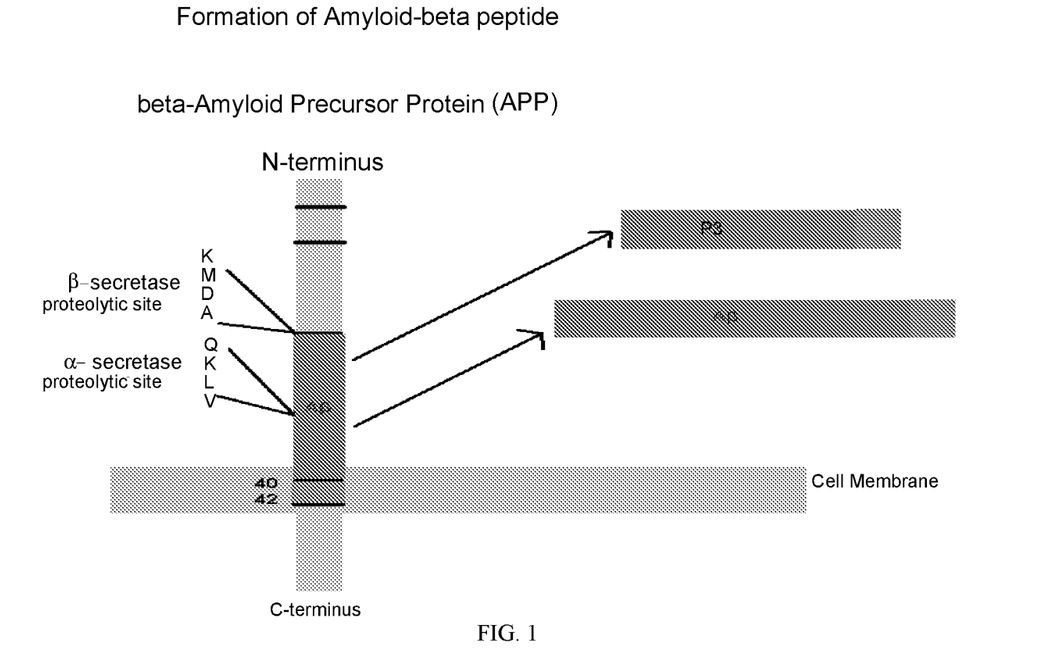
FIG. 1 shows the processing of beta amyloid peptide in the brain from amyloid precursor protein (APP)

As illustrated in FIG. 1, the APP protein located transmembranal within plasma membrane and spanned from cytoplasm into the surrounding extracellular space. Post-translational processing of APP involves several secretase enzymes to cleave APP into smaller polypeptides. It is normal for a healthy person to have some beta amyloid peptide in his/her cerebrospinal fluid (CSF) and bloodstream as these peptides may diffuse out or be actively transported out from the brain; however people with AD have a pathologic accumulation of the beta amyloid peptide within their brains and are unable to excrete the peptide from the brain.

Figure 2:
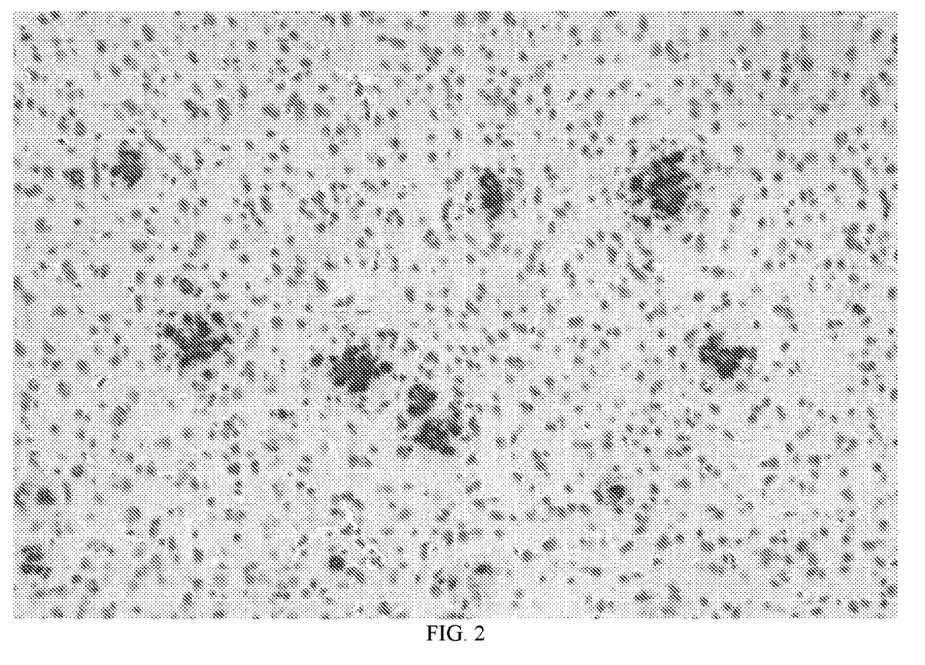
FIG. 2 shows the senile neuritic plaques of beta amyloid.

FIG. 2 shows the pathologic appearance of beta amyloid peptide in the brain of persons with AD. As AD progresses, the beta amyloid peptide aggregates into fibrils and becomes deposited as insoluble precipitate in senile neuritic plaques, which may be stained histochemically and be detected using magnetic resonance imaging (MRI).

Amyloid beta (Aβ) found to be the primary constituent of fibrils in the extraneuronal senile neuritic plaques of Alzheimer's patients' brains. It is believed that the mature fibrils of Aβ peptide are not neurotoxic per se, but may serve as a reservoir of small, diffusible soluble oligomers of Aβ. It has been shown that cortical levels of soluble Aβ correlate with both the extent of synaptic loss and severity of the clinical symptoms.

$A\beta_{40}$ and $A\beta_{42}$ are two common isoforms of the peptide where $A\beta_{42}$ is more fibrillogenic, aggregates more quickly, and higher toxicity especially in the dimer state. Aβ has little toxicity while in the monomeric state. Therefore, inhibiting formation of soluble Aβ dimers will nullify the neurotoxicity and be effective in preventing and/or treating Alzheimer's disease.

Previous research has discovered that the addition of soluble Aβ dimers to rodent hippocampal slices will potently inhibit long-term potentiation (LTP), enhance long-term depression (LTD), and reduce the neuronal dendritic spine density in the normal rodent hippocampus. These soluble Aβ dimers are also known to interfere with memory of learning behavior in rodents' brains.

Shankar's lab showed that the level of soluble Aβ-dimers is correlated to the clinical Alzheimer's disease state and the degree of progression of the dementia. It is known that the hippocampus is important in memory formation and consolidation, the pathologic appearance of amyloid plaques correlates well with the progression of Alzheimer's disease and the concomitant memory and cognitive losses. Clearance of these soluble Aβ dimers from the brain will ameliorate the cognitive deficits. Researchers have theorized that dementia is resulted from clearance of soluble Aβ dimers in the brain.

It has also demonstrated that soluble Aβ dimers interfere with glutamatergic synaptic transmission, where mGluRs are necessary for LTD induction. The data shows interference of soluble Aβ dimers with the NMDARs (N-methyl-D-aspartate receptors) is required for neuronal dendritic spine losses.

Multiple studies have shown that the soluble assemblies of oligomeric Aβ are the neurotoxic species which cause the cognitive losses of Alzheimer's disease. These oligomeric Aβ(oAβ) have also been called Aβ-derived diffusible ligands (ADDLs). Recent research has shown that the oAβ/ADDLs play a key role in cognitive decline.

Direct injection of oAβ/ADDLs into the hippocampi of live rats has caused cognitive and memory losses characteristic of Alzheimer's disease. Gandy has shown that the brain levels of oAβ/ADDLs correlate well with impaired acquisition of the Morris Water Maze (MWM) task by $APP^{E693Q}$ Q mice.

Selkoe's group has shown that Aβ dimers at subnanomolar concentrations directly induce Tau hyperphosphorylation, disruption of the microtubule cytoskeleton and neuritic degeneration in the rat hippocampus. Others have demonstrated that Aβ oligomers induce key characteristics of the AD phenotype including dendritic spine loss, altered hippocampal synaptic plasticity, and impaired memory for learned behaviors.

The hypothesis that small soluble oligomers of Aβ underlie the key phenotypic characteristics of Alzheimer's disease is supported by experimental data showing that these small soluble oligomers may: (1) cause synaptic loss and decreased dendritic spine density; (2) cause hyperphosphorylation of tau proteins with resulting intraneuronal neurofibrillary tangles and collapse of the neuritic cytoskeleton; (3) memory impairment and cognitive losses in the absence of amyloid plaques.

There are various ways AD diagnosis can be done; some of the examples are behavioral and cognitive testing, and an MRI of the brain. The presence of senile plaques in brain MRI is the indicator used in diagnostic of AD. These senile plaques are composed of fibrils of polymerized and precipitated beta amyloid. The aggregated oligomers and fibrils formed are neurotoxic and can caused neuronal cell death, thus it is speculated to be key events in the pathogenesis and progression of AD.

Most of the researches for Alzheimer's disease focus on preventing accumulation of beta amyloid peptide in the brain, which is believed to be a central event in the progression and pathogenesis of Alzheimer's disease. Some therapeutic strategies have been proposed, these strategies include but not limited to: (1) decreasing proteolytic production of Aβ through β-secretase inhibitors which block the first cleavage of APP in extracellular; (2) γ-secretase inhibitors which block the second cleavage of APP in the cell membrane; (3) increasing the clearance of soluble Aβ dimers through immunotherapy to induce antibody formation to amyloid beta; and (4) anti-aggregation drugs to inhibit the aggregation and polymerization of amyloid beta peptide.

Various natural plant-derived extracts or phytochemicals are being tested to look for natural agents to prevent polymerization of Aβ. Natural agents such as apple procyanidins, grape-derived polyphenols, Resveratrol and polyphenol curcumin (diferuloylmethane) are found to be inhibiting Aβ aggregation. Other polyphenol compounds which inhibit β-amyloid aggregation include: tannic acid, nordihydroguaiaretic acid, curcumin, rosmarinic acid, kaempferol, ferulic acid, (+)-catechin, (−)-epicatechin, and tetracycline. Blueberry-enriched polyphenols have been shown to prevent synaptic failure and adenosine triphosphate imbalance.

Flavonoids are also shown to have anti-aggregatory properties, examples like myricetin, chrysin, fisetin (3,3',4',7-tetrahydroxyflavone), 3',4',7-trihydroxyflavone, 3,3',4'-trihydroxyflavone, 3,3',7-trihydroxyflavone, 5-deoxykaempferol and synthetic derivatives. The glycosaminoglycan homotaurine (3-aminopropanesulfonic acid) also has anti-aggregation properties, however this compound has failed Phase III clinical trials in US and therefore it is no longer in use clinically.

Oil palm (*Elaeis guineensis*) has demonstrated various biological effects in treating diseases and improving health condition using palm oil and other palm-based materials such as palm oil vegetation liquor and oil palm phenolics.

Oil palm phenolics (OPP) is a complex aqueous derived from plant which mainly comprises polyphenol compounds, shikimic acid, oligosaccharides, and lipid. In addition, gallic acid, protocatechuic acid, p-hydroxybenzoic acid, vanillic acid, caffeic acid, syringic acid, p-coumaric acid and ferulic acid are also presence in OPP through high-performance liquid chromatography (HPLC), liquid chromatography-tandem mass spectrometry (LS/MS/MS) analyses. Five of the major polyphenol compounds are protocatechuic acid, p-hydroxybenzoic acid, 3-caffeoylshikimic acid, 4-caffeoylshikimic acid, and 5-caffeoylshikimic acid. These polyphenol compounds are known to have significant antioxidant properties as assayed by the DPPH (2,2-diphenyl-1-picrylhydrazyl) assay as well as the GAE (Gallic Acid Equivalent) assays.

Our prior research has demonstrated the neuroprotective effects of OPP in specific strains of mice, and therefore it is an object of present invention to disclose the efficiency of OPP in impeding or inhibiting the aggregation of Aβ into the neurotoxic soluble Aβ dimers or oligomers in vitro.

The present invention discloses OPP containing some active compounds that inhibit the aggregation of amyloid beta peptide and thus reduce the polymerization of the peptide. This inhibition may cause the beta amyloid peptide to remain in the soluble monomeric state and facilitate the clearance of the peptide from the brain via the normal physiologic mechanisms. Therefore, it is an object of present invention to provide a compound in preventing or slowing the progression of Alzheimer's disease.

Further objects and advantages of the present invention may become apparent upon referring to the preferred embodiments of the present invention as shown in the accompanying drawings and as described in the following description.

SUMMARY OF THE INVENTION

The present invention discloses a composition comprising oil palm phenolics (OPP), wherein said composition is useful in preventing or treatment of Alzheimer's disease and diseases related thereto. The composition is useful in impeding aggregation of β-amyloid into neurotoxic Aβ-dimer. The composition is also useful in impeding polymerization of β-amyloid, impeding folding of β-pleated sheet secondary structure in β-amyloid peptide and inhibiting kinetic accumulation of the β-pleated sheet amyloid peptide.

The present invention can be used in preparation of a medicament in a therapeutic effective amount for prevention or treatment of Alzheimer's disease and diseases related thereto in an individual in need thereof, which may be administered orally, conventional treatment forms, pharmaceutical formulations, nutritional supplement or as nutraceutical supplement.

BRIEF DESCRIPTION OF THE DRAWINGS

These and other features, aspects, and advantages of the present invention will become better understood with regard to the following description, appended claims, and accompanying drawings, in which:

DETAILED DESCRIPTION OF THE INVENTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Present invention provides oil palm phenolics (OPP) which constitutes a water soluble extract from the palm fruit (*Elaeis guineensis*) and are effective in treating Alzheimer's disease (AD) through inhibiting of beta amyloid peptides aggregation. The efficiency of this compound is validated by Mass Spectroscopy, Congo Red Binding Assay, and 2D-IR spectroscopy. These results demonstrate the anti-Alzheimer activity of OPP providing initial evidence towards its potential therapeutic uses.

Best Mode For Carrying Out The Invention

The method of preparation and use of the present invention is further illustrated by the following experimental examples. It should be understood that these experimental examples, while indicating preferred embodiments of the invention, are given by way better elucidation only. A person skilled in the art can ascertain the essential characteristics and embodiments of this invention, therefore various changes may be provided to adapt to various usages and conditions.

Materials and Methods

Preparation of Oil Palm Phenolics

OPP is a vegetation liquor which is prepared from the oil-bearing palm fruit (*Elaeis guineensis*), by a proprietary method established by the Malaysian Palm Oil Board (MPOB) as described in the U.S. Pat. No. 7,387,802. Briefly, oil palm fruits are crushed and squeezed mechanically, followed by removal of undissolved solids, oleaginous parts, colloids and higher molecular weight molecules from the remaining vegetation liquor which is an aqueous fraction containing phytochemicals. Oil palm phenolics comprise phytochemicals include but not limited to polyphenols, flavonoids, phenolic acids, hydroxyl acids, oligosaccharides, lipids (fatty acids and oils), shikimic acid and metal ions.

β-Amyloid Peptide Sample Preparation

Predetermined amount of lyophilized β-amyloid powder was redissolved in 50 ml of DMSO (dimethylsulfoxide) and 950 ml of PBS (phosphate-buffered saline, 10 mM, pH 7.4). Predetermined amount of lyophilized Ab42 powder was pretreated and resolubilized with 69.5 µl of a mixture comprising of $CH_3CN$/300 mM $Na_2CO_3$/250 mM NaOH (48.3:48.3:3.4, v/v/v). The resulting alkaline Ab42 solution (500 µM) was diluted 1:10 with phosphate buffer (10 mM, pH 7.7) containing NaCl (11 mM) to obtain a 50-µM Ab42 solution at pH 8.0 and NaCl concentration of 10 mM.

The final assay conditions were as follows: 50 µM Ab42 in phosphate buffer (8.7 mM) containing 10 mM NaCl, 14.5 mM $Na_2CO_3$, 0.85 mM NaOH, and 8.2% ACN (acetonitrile, pH 8.0). The Ab42 solutions were incubated at 30° C. without any stirring. Analyses were then performed at selected times.

Aβ42 Aggregation Inhibition Studies (Congo Red Binding Assay)

This inhibition study was initiated by incubating Ab42 samples at 30° C. in assay variables of with and without OPP. The Ab42 samples are incubated without any stirring. OPP used in this study was solubilized in water at a stock concentration of around 9%. In time course experiments, OPP stock solution was diluted in assay buffer to a final concentration of approximately 1.78% under assay conditions ([OPP]/[Ab42]=1:5). Initially, aliquots of stock solution were added to the Ab42 samples before incubation at 40° C. The inhibitory values were read and recorded. $IC_{50}$ (half maximal inhibitory concentration) of this study was calculated by dividing the full range of inhibitory values in half.

Thioflavin-T Fluorescence Assay

Thioflavin-T (ThT)-based fluorometric assays were performed with a spectrofluorometer using 96-well microtiter plates. The solution containing Ab42 (50 µM) or Ab42 in the presence of ThT (1.5 µM) up to a final volume of 2.0 ml is subjected to time scan in spectrofluorometer after incubation. The exciting emission was at a wavelength of 450 nm and the fluorescence emission signal was monitored at 535 nm (kex=446 nm). The fluorescence intensity values at the plateau (300 s) were averaged after subtracting the background fluorescence from 1.5 µM ThT and tested compound.

Although the ThT is a well-known and well-used assay for beta amyloid peptide aggregation, it is not possible to be used with OPP due to its strong fluorescent signal that overlaps with fluorescent signal from ThT. Thus ThT experiments were performed to examine the kinetics of beta amyloid peptide aggregation in the absence of OPP.

Congo Red Binding Assay

The stock solution of Ab42 (50 µM) was added into predetermined amount of OPP or phosphate buffer before diluted to a final concentration of 10 µM. The mixture is incubated and added with 64 of Congo Red dye. The Congo Red binding assays were performed with microplate reader and 96-well microtiter plates. The absorption readings were monitored at both wavelength of 492 nm and 540 nm, this is because the spectral shift occurs when Congo Red is bound to aggregated beta amyloid peptide. The data is then used to generate a bound Congo Red curve as described later on.

Mass Spectroscopy by MALDI-TOF

Mass spectroscopy is useful in detecting and quantitating the molecular weights of polypeptides and their aggregates.

The location and size of the peaks observed correlate well with the molecular weight and the quantity of substance present.

The analysis was performed by spotting on the target plate with 1.0 µl of the sample mixed with an equal volume of the matrix solution, 10 mg/ml sinapinic acid, in $CH_3CN/H_2O$ (50:50, v/v) containing 0.1% (v/v) trifluoroacetic acid. 10 µl of the sample was C4 ziptipped, eluted in 1 µl of 70% ACN (acetonitrile), mixed with 1 µl of matrix, spotted, and allowed to air dry.

Ab42 MALDI-TOF (matrix-assisted laser desorption ionisation-time of flight) mass spectrometry analyses were performed using a MALDI-TOF mass spectrometer equipped with a pulsed nitrogen laser operating at 337 nm. Small oligomer positive ion spectra were acquired in linear mode over an m/z range from 2000 to 50,000 using a 20-kV accelerating voltage and a 150-ns delay extraction time. The spectrum for each spot was obtained by averaging the results of 200 laser shots.

2-D FTIR Assay

Equilibrium Measurements

Analogous to nuclear magnetic resonance (NMR) spectroscopy, two-dimensional infrared spectroscopy (2DIR) reveals structural information onto two frequency axes and correlating the frequency of initial vibrational excitation ($\omega_1$) with a final detection frequency ($\omega_3$). The frequencies of the diagonal peaks correspond to the vibrational transitions within the sample, and cross peaks are only observed when two vibrational modes are coupled (i.e. if the modes reside within the same structure or if there is energy transfer between two vibrations). In a 2DIR spectrum, each positive diagonal peaks is accompanied by a negative appearing below the diagonal, these negative peaks are from vibrational transitions involving two-quanta states and contain information related to the anharmonicities of the individual modes.

Amyloid-beta samples were prepared in D2O at a concentration of 10 mg/ml and buffered to a final pH of 7.4 in a 10 mM deuterated phosphate and held between CaF2 windows in a 50 µm path-length cell. Spectra were collected in the perpendicular (ZZYY) polarization geometry to enhance the intensity of the cross peak.

Description of Spectra

In the amide-I region, beta-sheets are characterized by the presence of two peaks centered near 1620 and 1680 $cm^{-1}$, whose individual amide oscillators vibrate in-phase perpendicular ($v_\perp$) or parallel ($v_{81}$) to the β-strands, respectively. The splitting between these modes and the frequency of $v_|$ in particular are related to the size of the folded (β-sheet. In a primarily (β-sheet protein and the corresponding cross peaks give a characteristic Z-shape to the spectrum. Present invention focuses on the cross peak centered at [w1, w3]= [1620, 1680] $cm^{-1}$ whose amplitude which indicates the total amount of β-sheet present in the sample.

Figure 7A:
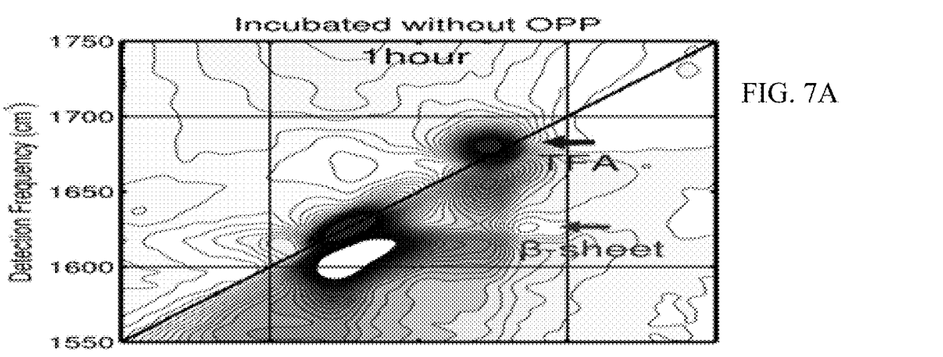
FIGS. 7A and 7B show the amide-I two-dimensional correlation spectra of the beta-amyloid samples incubated at 37° C. without OPP for 1 hour and 10 hours respectively.
Figure 7B:
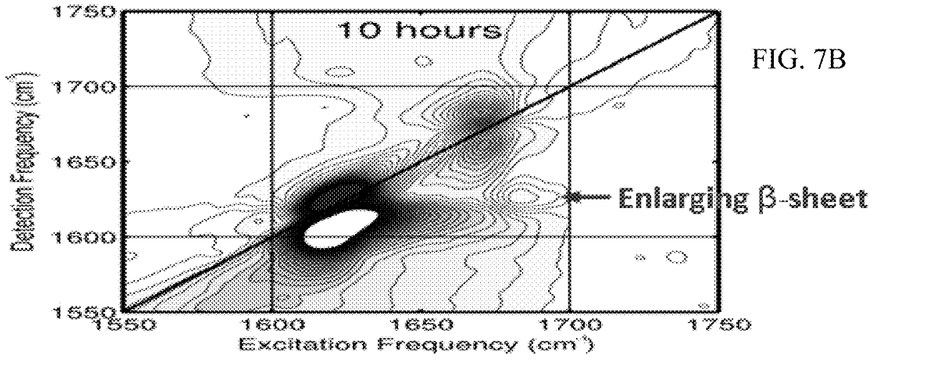
Figure 7C:
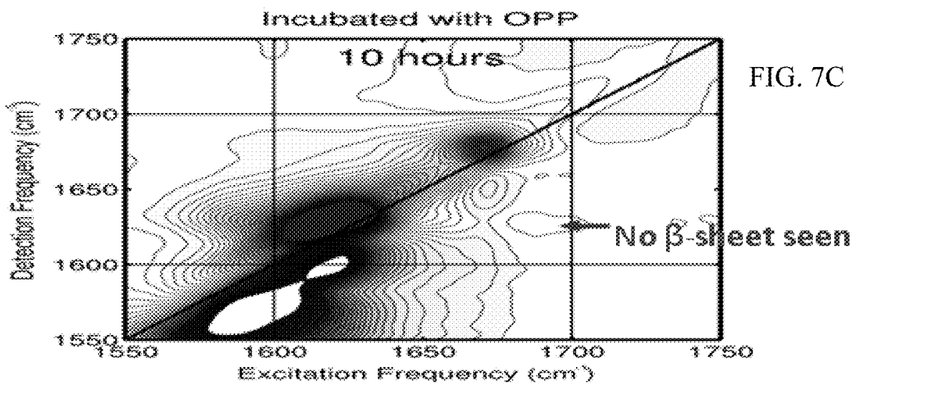
FIG. 7C shows the amide-I two-dimensional correlation spectra of the beta-amyloid samples incubated at 37° C. with OPP for 10 hours.

As shown in the experimental spectra on FIGS. 7A, 7B, and 7C, the $v_{ii}$ peak is masked by a strong diagonal peak at 1672 $cm^{-1}$, arising from the carbonyl stretch in tetrafluoroacetic acid (TFA), a compound used to cleave the peptide during the solid-state synthesis. TFA is particularly difficult to remove since lyophillization causes beta-amyloid aggregation. Since TFA does not have any other transitions in the CO stretching region, the off-diagonal features observed in the spectrum are only possible to cause by β-sheet structure. This describes the ability of 2DIR spectroscopy in extracting structural information even when the IR transitions of interest are masked by other species present in solution.

The three spectra shown in FIGS. 7A, B, and C are corresponded to the amyloid-beta sample incubated for a period of 1 hour and 10 hours at 37° C. in the absence of OPP, as well as incubated with OPP for 10 hours at 37° C. respectively. The spectra show that the cross peak at [w1, w3]=[1620, 1680] $cm^{-1}$ (indicated by arrow) increases in amplitude over this period. The increase in amplitude relates to an overall increase in β-sheet content of the sample as well as the increase in growth of β-fibrils in within the sample.

Previous studies have shown that increasing incubation duration will not affect amplitude of the cross peak. FIG. 7C shows sample incubated with OPP resulting in a very small cross peak even after incubation for 10 hours. In FIGS. 7A and 7B, the diagonal peaks associated with β-sheet become significantly broader and signal near the 1650 $cm^{-1}$ region increases. Part of the spectrum is associated with helical and random-coil conformations, the absence of signal in FIG. 7C suggesting that OPP disrupts the secondary structure of amyloids, and thus preventing the formation of β-fibrils.

The 2DIR spectrum correlates the frequency of initial vibrational excitation ($\omega_1$) with a final detection frequency ($\omega_3$). The frequencies of diagonal peaks can be assigned to chemically distinct vibrational modes. The presence and splitting of cross-peaks characterizes the anharmonic coupling of the vibrations and helps decompose congested spectra. Present invention concentrates on the diagonal and cross-peaks between two vibrational bands of β-sheets ($v_\perp$ and $V_\parallel$), whose individual amide oscillators vibrate in-phase perpendicular or parallel to the β-strands, respectively. The splitting between these modes and the frequency of $v_\perp$ in particular are indicators of the size of the folded β-sheet and provide an important signature in transient experiments.

Absorptive spectra were acquired with parallel (ZZZZ) and perpendicular (ZZYY) probing polarizations. For β-amyloid, the $v_\perp$ and $v_\parallel$ β-sheet modes are observed on 1620 $cm^{-1}$ and 1680 $cm^{-1}$ regions of the amide I spectrum.

At 63° C., inhomogeneous broadening causes the two transitions to be not clearly resolved but appear as a broad diagonal peak both for the fundamental transition (v=0→1, positive) and for the overtone transition (v=1→2, negative). The overtone transition lies below the fundamental along the $\omega_3$ axis because of the anharmonicity of the vibrational potential. The $v_|$ and $v_\parallel$ modes have nearly orthogonal transition moments where the cross-peaks are small in the parallel polarization geometry but are enhanced and form a cross-peak ridge in the upper left corner in the perpendicular polarization geometry. Loss of negative intensity (a positive change) in the lower right corner also indicates the presence of a positive cross-peak in this region. The overall Z-shape of the perpendicular spectrum, which arises from interference effects between $v_|$ and $v_\parallel$ diagonal and cross-peaks, is a characteristic signature of the β-sheet structure.

Results

The mass spectrograms show that the beta amyloid peptide tend to spontaneously form aggregates consisting of dimers, trimers, tetramers, pentamers and higher order aggregates. In reference to FIGS. 3, 4A and 4B, the presence of OPP impedes the aggregation process of beta-amyloid peptide, and mostly the monomer beta amyloid peptide is observed without the higher order aggregates.

Tabulation of Peak Aggregates Observed by Mass Spectroscopy

Figure 3:
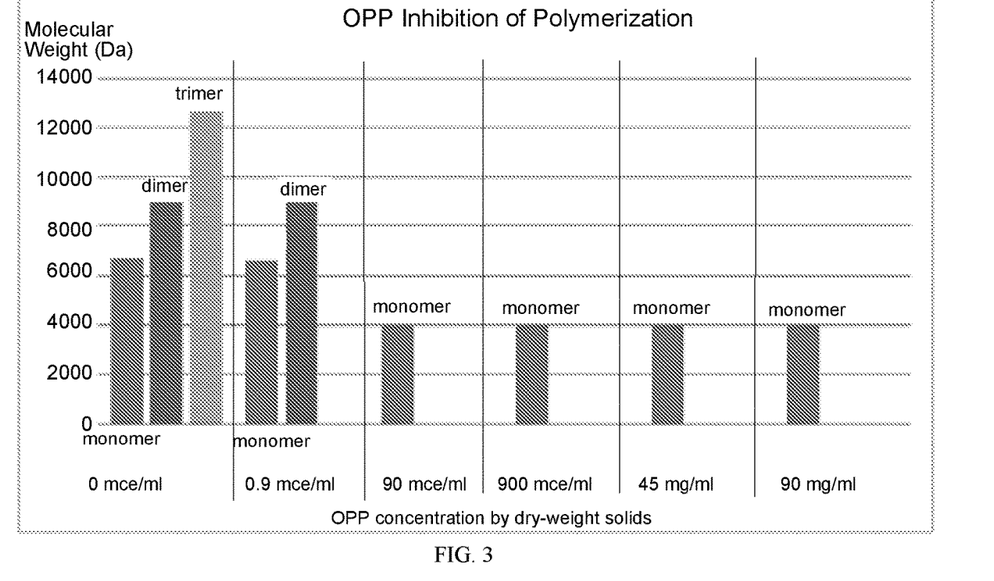
FIG. 3 shows the effect on molecular weights of beta amyloid peptide over time after treatment with oil palm phenolics (OPP)

The molecular weights of the beta amyloid peptide and its aggregates with or without the presence of OPP are shown in FIG. 3. There are 3 species of peptides found in sample absence of OPP (0 mcg/ml) namely, monomer, dimer and trimer. At concentration of 0.9 mcg/ml OPP, only the monomer and dimer peptides are found. From the concentration of 90 mcg/ml up to 90 mg/ml, only monomer of beta amyloid peptide is found.

Figure 4A:
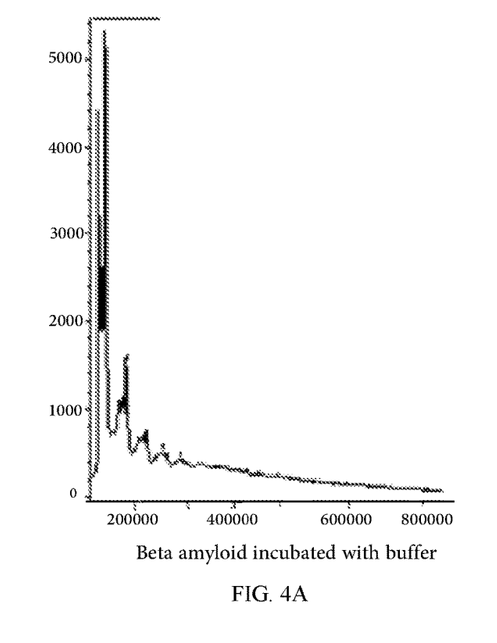
FIG. 4A shows the effect on beta amyloid peptide aggregation after treatment without OPP.
Figure 4B:
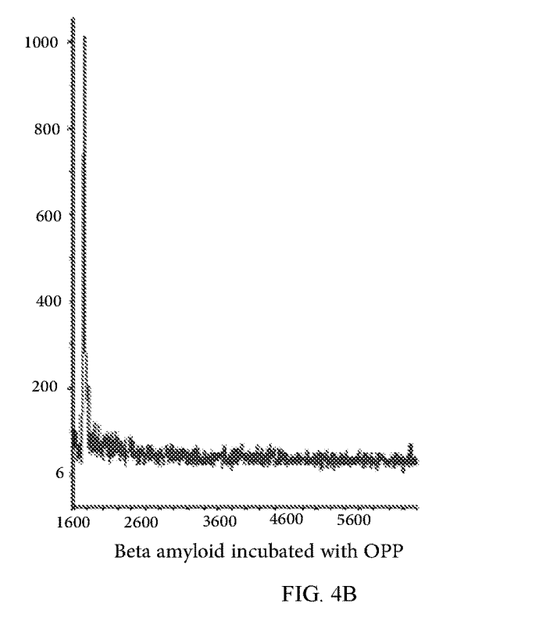
FIG. 4B shows the effect on beta amyloid peptide aggregation after treatment with OPP.

FIGS. 4A and 4B show the raw data mass spectrograms of beta amyloid peptide aggregation assay generated from the MALDI-TOF apparatus. FIG. 4A shows beta amyloid peptides are aggregated up to septamers with molecular weight of 31.5 kDa (7 peptides) in the absence of OPP, whereas in FIG. 4B only the monomer (4.5 kDa) of beta amyloid is observed in the presence of OPP.

Inhibition of Beta Amyloid Peptide Aggregation by OPP

Beta amyloid peptide is incubated in PBS at 37° C. and maintained at pH 7.4. FIG. 4A shows the aggregates of several molecular size forms, i.e. dimers, trimers, pentamers, hexamers and septamers, whereas in FIG. 4B addition of OPP at a concentration of 0.9 mg/ml into the previous condition inhibits the peptides from aggregating and remains in the monomeric form. The mass spectroscopy data clearly shows that the presence of OPP will inhibit the aggregation and polymerization of beta amyloid peptide.

Thioflavin-T Dye Assay of Aggregation Dynamics and the Auto-Fluorescence of Oil Palm Phenolics Thioflavin-T assay is performed to observe the normal aggregation kinetics of the beta-amyloid peptide in the absence of OPP.

Figure 5:
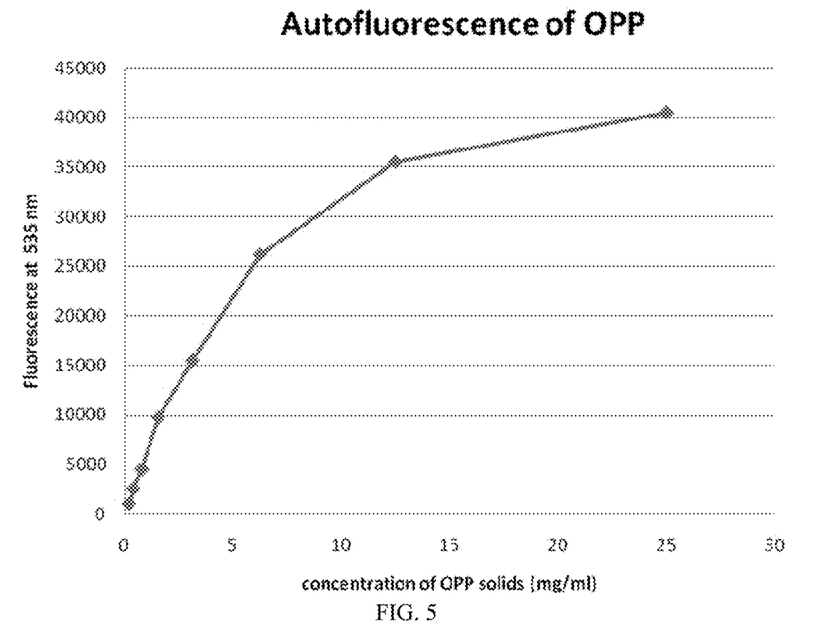
FIG. 5 shows the fluorescence spectrogram of OPP at wavelength of 535 nm.

FIG. 5 shows a spectrogram of titrated concentrations of OPP fluorescing at a wavelength of 535 nm as similar to many antioxidant polyphenols.

The fingerprinting analysis of OPP (Sambandan et al.) reveals 5 "signature" polyphenols present in OPP. These include p-hydroxybenzoic acid, protocatechuic acid, and 3 structural isomers of caffeoylshikimic acid. Based upon their spectroscopic properties, these 5 polyphenol components of OPP most probably account for the strong autofluorescence observed at a wavelength of 535 nm.

Due to the strong autofluorescence of the OPP, it was not feasible to conduct aggregation or kinetic experiments on the β-amyloid peptide with "noise" of OPP fluorescence 3-4 times of higher magnitude than the fluorescent signal generated by the Thioflavin-T bound to aggregates.

Congo Red Binding Assay

The Congo Red assay is based on the spectral shift occurs in the absorption of Congo Red bounded to beta amyloid peptide aggregates or fibrils at 2 different reference wavelengths.

Figure 6:
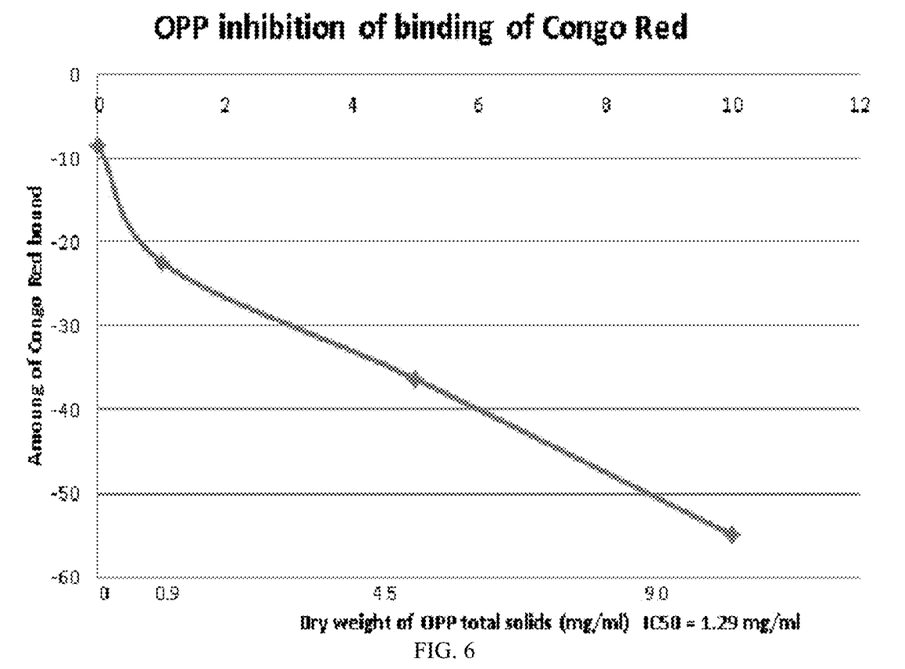
FIG. 6 shows the Congo red dye binding curve at various concentrations of OPP.

In reference to FIG. 6, the dilution of OPP is directly proportional to the amount of Congo Red bound to the peptide aggregates and oligomers. An inverse linear relationship between the amount of OPP solids and the quantity of beta amyloid aggregates can be observed. The degree of Congo Red binding relates to beta amyloid peptide aggregation, also show that OPP inhibits the aggregation and polymerization of beta amyloid peptide.

$IC_{50}$ provides a good indication for the efficacy of inhibiting beta amyloid peptide aggregation by OPP. Based on FIG. 6 OPP inhibition of Congo Red binding data, the $IC_{50}$ is 1.29 mg/ml of total solids by dry weight, at which point 23.22% of Congo Red is bound to aggregates.

Congo Red dye binds directly to the beta amyloid peptide and resulting in spectral shift when Congo Red bounded to aggregated peptide as opposed to monomeric peptide. The quantitation of aggregated beta amyloid peptide is given by the formula: $Cb = A_{541}/47,800 - A_{403}/38,100$ where Cb represents the amount of Congo Red dye bound to aggregated peptide, $A_{541}$ and $A_{403}$ are the optical absorptions measured at the wavelength of 541 nm and 403 nm respectively, 478000 and 38100 are the extinction coefficients at 541 nm and 403 nm respectively.

2DIR Results

FIGS. 7A, 7B and 7C show the Amide-I two-dimensional correlation spectra of the beta-amyloid samples incubated at 37° C. with and without OPP. The diagonal peak at 1672 $cm^{-1}$ is due to tetrafluoroacetic acid (TFA) present in the sample. The cross-peak near [w1, w3]=[1620, 1680] $cm^{-1}$ is due the beta-fibrils. FIG. 7C shows broader peaks and a weaker cross peak which indicates lower beta-fibril content.

From the results as disclosed in the description, OPP is shown to substantially impeding the aggregation of Aβ peptide into dimers by Mass Spectroscopy, 2DIR spectroscopy and Congo Red dye binding assay. However, the active phytochemical agents in OPP that are useful in inhibiting formation of neurotoxic Aβ-dimers in present invention should not be limited to one type.

From the result obtained from Congo Red binding assay, the $IC_{50}$ (half-maximal inhibition) for OPP against beta amyloid peptide aggregation is approximately 1.29 mg/ml. The usual concentration of OPP is 9.0% solids, thus the concentration of solids is 90 mg/ml. The $IC_{50}$ of 1.29 mg/ml is therefore a dilution of 1.43% of OPP (or a 1:70 dilution of the OPP).

In addition, Mass Spectroscopy has provided very useful data showing the aggregation of the beta amyloid peptide monomer by revealing the molecular weights of the peptide species present. FIGS. 4A AND 4B shows the efficiency of OPP in impeding beta amyloid peptide aggregation where amyloid-beta peptide aggregates and polymerize in the absence of OPP (FIG. 4A) and amyloid-beta peptide remains monomeric in the presence of OPP (FIG. 4B).

The 2DIR spectroscopy also discloses the efficiency of OPP in inhibiting (β-amyloid peptide from misfolding into beta-pleated sheets on secondary structure. In the absence of OPP, the kinetic accumulation of the beta-pleated sheet amyloid peptide is shown in 2DIR spectroscopy, whereas in the presence of OPP there is no formation of beta-pleated sheet structures.

Efficacy in maintaining beta amyloid peptide in soluble form and preventing peptide from aggregating into insoluble polymers or fibrils may be important feature for a drug in prevention or treatment of Alzheimer's disease. The peptides maintained in soluble form would allow excretion with body's normal clearance mechanisms before it could fibrillize into the senile neuritic plaques, and therefore preventing occurrence of Alzheimer's disease.

It is possible that OPP binds to beta amyloid peptide, and prevents the hydrogen-bonding and hydrophobic interactions from polymerizing peptide in forming aggregated fibrils. 2DIR spectroscopic are conducted to elucidate the secondary and tertiary structure of this interaction between OPP and beta amyloid peptide.

The study of kinetics of aggregation for the 42-amino acid β-amyloid peptide shows that (1) OPP impede β-amyloid monomers from aggregating and polymerizing into larger aggregates as shown by the decrease in molecular weights measured on Mass Spectroscopy; (2) OPP inhibit binding of Congo Red dye to β-amyloid peptide as shown by the decrease in Congo Red dye binding to aggregated β-amyloid peptide; (3) OPP impede folding of β-pleated sheet secondary structures, as revealed by 2DIR Spectroscopy.

It is well established that the soluble β-amyloid dimers and oligomers cause extensive pathologic changes in neurons, decrease dendritis spine density, and cause depression of long-term potentiation in neurons and enhancement of long-term depression. Therefore, the inhibitory, anti-aggregatory, and antifibrillogenic properties of OPP may lead to the development of a potential drug for the prevention or treatment of Alzheimer's disease.

The composition as disclosed in present invention may be provided as compounds with pharmaceutically acceptable carriers. Present invention further discloses the use of therapeutically effective amount of a composition in the preparation of a medicament for preventing or treatment of Alzheimer's disease or disease related thereto in an individual by administering to an individual in need thereof. The composition may be administered orally, conventional treatment forms, pharmaceutical formulations, nutritional supplement or as nutraceutical supplement.

It is understood by a person skilled in the art that the methods for experiments and studies are described as exemplifications herein and thus the results are not intended, however, to limit or restrict the scope of the invention in any way and should not be construed as providing conditions, parameters, agents, chemicals or starting materials which must be utilized exclusively in order to practice the present invention. It is therefore understood that the invention may be practiced, within the scope of the appended claims, with equivalent methods for the experiments than as specifically described and stated in claims.

The invention claimed is:

1. A method for inhibiting polymerization of β-amyloid peptides in an individual, the method comprising:
   administering a composition comprising 0.9 mcg/ml to 90 mg/ml of oil palm phenolics (OPP) to an individual to impede β-amyloid trimer aggregation, or administering a composition comprising 90 mcg/ml to 90 mg/ml of oil palm phenolics to an individual to impede β-amyloid trimer aggregation and β-amyloid dimer aggregation;
   wherein said OPP is derived from *Elaeis guineensis*, and said OPP comprises p-hydroxybenzoic acid, protocatechuic acid, three structural isomers of caffeoylshikimic acid, and shikimic acid; and
   wherein said composition is a pharmaceutical formulation, a nutritional supplement, or a nutraceutical supplement.

2. The method as claimed in claim 1, wherein administering the composition impedes folding of β-pleated sheet amyloid peptide.

3. The method as claimed in claim 1, wherein administering the composition prevents formation of neurotoxic Aβ-dimers.

4. The method as claimed in claim 1, wherein said administering the composition is orally administered.

\* \* \* \* \*